United States Patent
Mukaida et al.

(10) Patent No.: US 6,743,753 B2
(45) Date of Patent: Jun. 1, 2004

(54) HERBICIDAL COMPOSITIONS

(75) Inventors: Hideshi Mukaida, Moriya-machi (JP); Marc Montagnon, Cailloux sur Fontaines (FR); Jean Paviot, Saint Germain au Mont d'Or (FR)

(73) Assignee: Bayer CropScience S.A., Lyons (FR)

( * ) Notice: Subject to any disclaimer, the term of this patent is extended or adjusted under 35 U.S.C. 154(b) by 0 days.

(21) Appl. No.: 09/348,458

(22) Filed: Jul. 7, 1999

(65) Prior Publication Data

US 2001/0039245 A1 Nov. 8, 2001

(30) Foreign Application Priority Data

Jul. 8, 1998 (GB) .............................. 9814846

(51) Int. Cl.⁷ .................. A01N 47/36; A01N 57/02
(52) U.S. Cl. ............ 504/128; 504/116; 504/117; 504/128; 504/133; 504/134; 504/135; 504/132
(58) Field of Search ............... 504/116, 117, 504/128, 132, 133

(56) References Cited

U.S. PATENT DOCUMENTS 5,521,146 A 5/1996 Hur et al.
6,054,410 A 4/2000 Landes et al.

OTHER PUBLICATIONS

Landes, Max et al. (CA 126:260438, abstract of DE 19534910), 1997.*
Hur, Chang et al. (CA 123:228208, abstract of EP 658549), 1997.*

* cited by examiner

Primary Examiner—Sabiha Qazi
(74) Attorney, Agent, or Firm—Connolly Bove Lodge & Hutz LLP

(57) ABSTRACT

This invention relates to new herbicidal compositions comprising a mixture of (a) an alkoxypyrimidyloxybenzoic acid derivatives of formula (I):

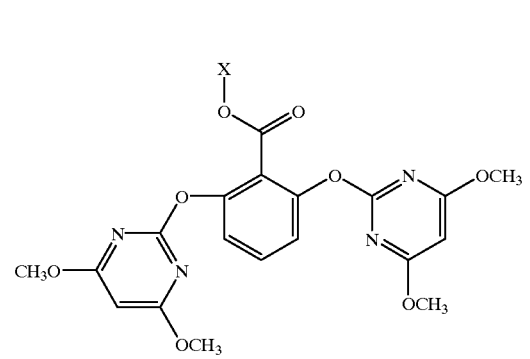

(I)

wherein X is a hydrogen atom or a group $(C_6H_5)_2C=N-$, or an agriculturally acceptable salts thereof, for example alkali or alkaline earth metal salts and (b) a partner herbicide. This invention additionally relates to a method of controlling weeds comprising applying these new herbicidal compositions to a locus.

36 Claims, No Drawings

HERBICIDAL COMPOSITIONS

This invention relates to new herbicidal compositions comprising a mixture of an alkoxypyrimidyloxybenzoic acid derivative and at least one partner herbicide. Additionally, this invention relates to a method of controlling weeds with the new herbicidal compositions comprising a mixture of an alkoxypyrimidyloxybenzoic acid derivative and at least one partner herbicide.

Pyribenzoxim, which is benzophenone O-{2,6-bis[(4,6-dimethoxypyrimidyl) oxy]benzoyl}oxime is known as a herbicide, see for example European Patent No. 658549.

Bispyribac is also known as sodium 2,6-bis[(4,6-dimethoxypyrimidin-2-yl)oxy]benzoate.

An object of the present invention is to provide a herbicidally effective mixture for increasing the efficacy of alkoxypyrimidyloxybenzoic acid derivatives, especially pyribenzoxims.

A further object of the present invention is to extend the spectrum of post-emergence herbicidal activity without loss of crop selectivity for an alkoxypyrimidyloxybenzoic acid derivative in combination with a partner herbicide, for example pyribenzoxim in combination with fenoxaprop-P. The term "combination" according to the invention as used in this specification refers to the "combination" of an alkoxypyrimidyloxybenzoic acid derivative and a partner herbicide.

Another object of the present invention is the selectivity of the combination of the invention.

A high level of control of many weeds is desirable to prevent:
1) yield loss, through competition from weeds and/or difficulties with harvest;
2) crop contamination leading to storage and cleaning difficulties; and
3) unacceptable weed seed return to the soil.

The present invention seeks to provide a herbicidal composition which allows lower dose rates of partner herbicides to be applied to the environment without reducing (and preferably increasing) the level of weed control.

A further object of the present invention is to provide a herbicidal composition which provides residual activity against weeds germinating after application, e.g., pyribenzoxim in combination with oxadiargyl.

The objects of the invention can be achieved in whole or part by the present invention.

The present invention provides a composition comprising:
(a) an alkoxypyrimidyloxybenzoic acid derivative of formula (I):

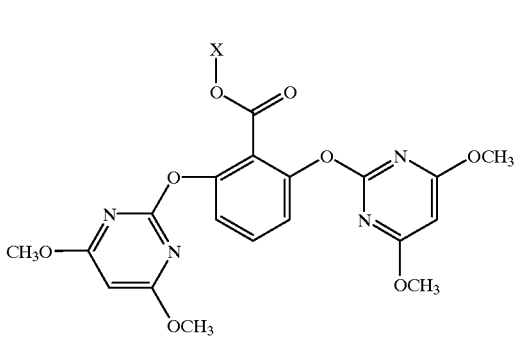

(I)

wherein X is a hydrogen atom or a group $(C_6H_5)_2C=N-$, and agriculturally acceptable salts thereof, for example alkali or alkaline earth metal salts and (b) a partner herbicide;
the amounts of a and b in combination being herbicidally effective, in association with an agriculturally acceptable diluent or carrier.

The alkoxypyrimidyloxybenzoic acid derivatives used in the invention are advantageously pyribenzoxim or bispyribac, preferably pyribenzoxim. Bispyribac is the compound of formula (I) wherein X is Na. Pyribenzoxim is the compound of formula (I) wherein X is $(C_6H_5)_2C=N-$.

Partner herbicides are preferably chosen from sulfonylureas, anilides, 2,6-dinitroanilines, carfentrazone, aryloxyphenoxy propionic acids, oxadiazoles, pyrimidyl salicylate, sulfamoylureas, thiocarbamates, hydroxybenzonitriles and pyrazoles.

Advantageous possible partner herbicides for use in the present invention include:

pendimethalin, which is [N-(1-ethylpropyl)-2,6-dinitro-3,4-xylidine];

bentazone, which is 3-isopropyl-1H-2,1,3-benzothiadiazin-4(3H)-one 2,2-dioxide;

butachlor, which is N-butoxymethyl-2-chloro-2',6'-diethylacetanilide;

pretilachlor, which is 2-chloro-2',6'-diethyl-N-(2-propoxyethyl)acetanilide;

oxadiargyl, which is 5 tert-butyl-3-[2,4-dichloro-5-(prop-2-ynyloxy)phenyl]-1,3,4-oxadiazol-2(3H)-one;

diflufenican, which is [2'-4'-difluoro-2-(α,α,α-trifluoro-m-tolyloxy) nicotinanilide;

bromoxynil, which is 3,5-dibromo-4-hydroxybenzonitrile;

ioxynil, which is 4-hydroxy-3,5-di-iodobenzonitrile;

propanil, which is 3',4'-dichloropropionanilide;

carfentrazone, which is ethyl 2-chloro-3-[2-chloro-4-fluoro-5-(4-difluoromethyl-4,5-dihydro-3-methyl-5-oxo-1H-1,2,4-triazol-1-yl)phenyl]propionate;

fenoxaprop, which is [(±)-2-[4-(6-chloro-1,3-benzoxazol-2-yloxy) phenoxy]propionic acid;

fenoxaprop-P, which is [(R)-2-[4-(6-chloro-1,3-benzoxazol-2-yloxy) phenoxy]propionic acid;

cyhalofop, which is butyl(R)-2-[4-(4-cyano-2-fluorophenoxy)phenoxy]propionate;

cyclosulfamuron, which is 1-[2-(cyclopropylcarbonyl) anilinosulfonyl]-3-(4,6-dimethoxypyrimidin-2-yl)urea;

pyributicarb, which is O-3-tert-butylphenyl 6-methoxy-2-pyridyl(methyl)thiocarbamate;

benzofenap, which is 2-[4-(2,4-dichloro-m-toluoyl)-1,3-dimethylpyrazol-5-yloxy]-4-'methylacetophenone;

cinosulfuron, which is 1-(4,6-dimethoxy-1,3,5-triazin-2-yl)-3-[2-(2-methoxyethoxy) phenylsulfonyl]urea;

bensulfuron, which is α-(4,6-dimethoxypyrimidin-2-ylcarbamoylsulfamoyl)-o-toluic acid;

pyrazosulfuron, which is 5-(4,6-dimethoxypyrimidin-2-ylcarbamoylsulfamoyl)-1-methylpyrazole-4-carboxylic acid;

imazosulfuron, which is 1-(2-chloroimidazo[1,2-a]pyridin-3-ylsulfonyl)-3-(4,6-dimethoxypyrimidin-2-yl)urea; and azimsulfuron, which is 1-(4,6-dimethoxypyrimidin-2-yl)-3-[1-methyl-4-(2-methyl-2-H-tetrazol-5-yl)-pyrazol-5-ylsulfonyl]urea.

The preferred partner herbicides are chosen from cyhalofop, fenoxaprop, fenoxaprop-P, bensulfuron, pyrazosulfuron, imazosulfuron, bentazone, benzofenap and oxadiargyl.

The most preferred mixtures are those comprising pyribenzoxim in combination with aryloxyphenoxy propionic acids or sulfonylureas or oxadiargyl. Preferred aryloxyphenoxy propionic acid herbicides are cyhalofop, fenoxaprop and fenoxaprop-P. Preferred sulfonylureas are bensulfuron or pyrazosulfuron or imazosulfuron.

According to another feature of the present invention, there is provided a method for controlling the growth of weeds, i.e. undesired vegetation, at a locus which comprises applying to the locus a herbicidally effective amount of a mixture comprising an alkoxypyrimidyloxybenzoic acid derivative of formula (I) and a partner herbicide as defined hereinabove.

The term 'post-emergence application' refers to application to the aerial or exposed portions of the weeds which have emerged above the surface of the soil. The term 'foliar activity' refers to herbicidal activity produced by application to the aerial or exposed portions of the weeds which have emerged above the surface of the soil. The term 'residual activity' refers to herbicidal activity produced by application to the soil in which weed seeds or seedlings are present before emergence of the weeds above the surface of the soil, whereby seedlings present at the time of application or which germinate subsequent to application from seeds present in the soil, are controlled.

Preferably, compositions of the present invention are applied to an area used, or to be used, for the growing of a crop, for example cereal crops, rice and wheat. The method of the invention is preferably performed where the crop to be protected is rice.

Weeds that may be controlled by this method include; *Echinochloa crus-galli, Leptochloa chinensis, Ischaemum rugosum, Sphenoclea zeylanica, Cyperus difformis, Cyperus iria, Cyperus seotinus,* Fimbristylis, *Monochoria vaginalis, Echinochloa colonum,* Sphenoclea, Eleocharis, *Marsilea, Saggitaria, Scirpus maritimus, Scirpus mucronatus* and Sesbania.

The amounts of alkoxypyrimidyloxybenzoic acid derivative of formula (I) and partner herbicide applied depend on many factors, including, but not limited to the weed species to be controlled, the crop present, the timing of the application and the climatic and edaphic conditions. When applied to a crop-growing area, the rate of application should be sufficient to control the growth of weeds without causing substantial permanent damage to the crop. In general, taking these factors into account, application rates from 0.005 kg to 0.2 kg preferably 0.005 kg to 0.1 kg of alkoxypyrimidyloxybenzoic acid derivative of formula (I) and 0.001 kg to 4 kg of partner herbicide per hectare give good results.

For the selective control of weeds at a locus of weed infestation which is an area used, or to be used, for growing of crops application rates from 5 g to 200 g of alkoxypyrimidyloxybenzoic acid derivative of formula (I) and from 1 g to 4000 g of the partner herbicide, per hectare are particularly suitable, preferably from 10 g to 100 g of alkoxypyrimidyloxybenzoic acid derivative of formula (I) and from 5 g to 2500 g of the partner herbicide per hectare, most preferably from 30 g to 80 g of alkoxypyrimidyloxybenzoic acid derivative of formula (I) and from 10 g to 1200 g of the partner herbicide per hectare. Preferably 0.1–200 g/ha aryloxyphenoxy propionic acid, 1–100 g/ha sulfonylurea or 20–200 g/ha oxadiargyl.

However, it is to be understood that higher or lower application rates may be used, depending upon the particular problem of weed control encountered.

In accordance with the usual practice (and a preferred method according to the present invention) a tank mix may be prepared prior to use by combining separate formulations of the individual herbicidal components.

According to a further feature of the present invention, there are provided compositions suitable for herbicidal use comprising an alkoxypyrimidyloxybenzoic acid derivative of formula (I) and a partner herbicide in association with, and preferably homogeneously dispersed in, one or more compatible agriculturally-acceptable diluents or carriers and/or surface active agents i.e. diluents or carriers and/or surface-active agents of the type generally accepted in the art as being suitable for use in herbicidal compositions and which are compatible with compounds of the present invention. The term "homogeneously dispersed" is used to include compositions in which the compounds of the present invention are dissolved in other components. The term "herbicidal compositions" is used in a broad sense to include not only compositions which are ready for use as herbicides but also concentrates which must be diluted before use. Preferably, the compositions contain from 0.05 to 90% by weight of one or more compounds of the present invention.

Unless otherwise stated, the percentages and ratios appearing in this specification are by weight, and in the case of salts, refer to the content of active ingredient in the salt. It will be understood that the partner herbicide may be in the form of an agriculturally acceptable salt.

Generally the weight ratio of alkoxypyrimidyloxybenzoic acid derivative of formula (I) to partner herbicide is from about 1:800 to about 200:1, preferably from about 1:250 to about 20:1, more preferably 1:40 to about 8:1.

The herbicidal compositions may contain both a diluent or carrier and surface-active (e.g. wetting, dispersing, or emulsifying) agent. Surface-active agents which may be present in herbicidal compositions of the present invention may be of the ionic or non-ionic types, for example sulphoricinoleates, quaternary ammonium derivatives, products based on condensates of ethylene oxide with alkyl and polyaryl phenols, e.g. nonyl- or octyl-phenols, or carboxylic acid esters of anhydrosorbitols which have been rendered soluble by etherification of the free hydroxy groups by condensation with ethylene oxide, alkali and alkaline earth metal salts of sulphuric acid esters and sulphonic acids such as dinonyl- and dioctyl-sodium sulphonosuccinates and alkali and alkaline earth metal salts of high molecular weight sulphonic acid derivatives such as sodium and calcium lignosulphonates and sodium and calcium alkylbenzene sulphonates.

Suitably, the herbicidal compositions according to the present invention may comprise up to 10% by weight, e.g. from 0.05% to 10% by weight, of surface-active agent but, if desired, herbicidal compositions according to the present invention may comprise higher proportions of surface-active agent, for example up to 15% by weight in liquid emulsifiable suspension concentrates and up to 25% by weight in liquid water soluble concentrates.

Examples of suitable solid diluents or carriers are aluminium silicate, microfine silicon dioxide, talc, chalk, calcined magnesia, kieselguhr, tricalcium phosphate, powdered cork, adsorbent carbon black and clays such as kaolin and bentonite. The solid compositions (which may take the form of dusts, granules or wettable powders) are preferably prepared by grinding the compounds of the present invention with solid diluents or by impregnating the solid diluents or carriers with solutions of pyribenzoxim and partner pesticides in volatile solvents, evaporating the solvents and, if necessary, grinding the products so as to obtain powders. Granular formulations may be prepared by absorbing the compounds of the present invention (dissolved in suitable solvents, which may, if desired, be volatile) onto the solid diluents or carriers in granular form and, if desired, evaporating the solvents, or by granulating compositions in powder form obtained as described above. Solid herbicidal compositions, particularly wettable powders and granules, may contain wetting or dispersing agents (for example of the types described above), which may also, when solid, serve as diluents or carriers.

Liquid compositions according to the invention may take the form of aqueous, organic or aqueous-organic solutions, suspensions and emulsions which may incorporate a surface-active agent. Suitable liquid diluents for incorporation in the liquid compositions include water, glycols, glycol ethers, tetrahydrofurfuryl alcohol, acetophenone, cyclohexanone, isophorone, N-alkyl pyrrolidones, toluene, xylene, mineral, animal and vegetable oils, esterified vegetable oils and light aromatic and naphthenic fractions of petroleum (and mixtures of these diluents). Surface-active agents, which may be present in the liquid compositions, may be ionic or non-ionic (for example of the types described above) and may, when liquid, also serve as diluents or carriers.

Powders, dispersible granules and liquid compositions in the form of concentrates may be diluted with water or other suitable diluents, for example mineral or vegetable oils, particularly in the case of liquid concentrates in which the diluent or carrier is an oil, to give compositions ready for use.

When desired, liquid compositions of alkoxypyrimidyloxybenzoic acid derivatives of formula (I) and partner herbicides may be used in the form of self-emulsifying concentrates containing the active substances dissolved in the emulsifying agents or in solvents containing emulsifying agents compatible with the active substances, the simple addition of such concentrates to water producing compositions ready for use.

Liquid concentrates in which the diluent or carrier is an oil may be used without further dilution using the electrostatic spray technique.

Herbicidal compositions according to the present invention may also contain, if desired, conventional adjuvants such as adhesives, protective colloids, thickeners, penetrating agents, spreading agents, stabilisers, sequestering agents, anti-caking agents, colouring agents and corrosion inhibitors. These adjuvants may also serve as carriers or diluents.

The method of the invention is preferably applied post-emergence to the weeds and to the crop plant.

The invention also provides a product comprising an alkoxypyrimidyloxybenzoic acid derivative of formula (1), or an agriculturally acceptable salt thereof, and a partner herbicide, for simultaneous, separate or sequential application in controlling the growth of weeds The following non-limiting examples illustrate the invention.

EXAMPLE 1

Seed of various weed species were sown and grown up to a 2–4 leaves stage. The said weeds are *Echinochloa crusgalli* (hereafter ECGCH), *Leptochloa chinensis* (hereafter LEFCH), *Monochoria vaginalis* (hereafter MOOVA) and *Cyperus difformis* (hereafter CYPDI).

Mixtures of pyribenzoxim and a partner herbicide were applied post emergence in a water diluted form using a laboratory sprayer. A visual assessment was made 28 days after treatment (DAT).

In the tables that follow 'dose' represents the dose rate in grammes per hectare of the active ingredient used; the figures for the weed control are percentage reductions in growth when compared with untreated controls; and CpdA represents pyribenzoxim.

Results

TABLE 1

Post-emergence treatment of ECGCH with various mixtures of pyribenzoxim and bensulfuron.

| CpdA | bensulfuron | | | |
|---|---|---|---|---|
| Dose | 0 | 6.5 | 13 | 25 |
| 0 | 0 | 30 | 50 | 70 |
| 7.5 | 20 | 60 | 80 | 95 |

TABLE 2

Post-emergence treatment of LEFCH with various mixtures of pyribenzoxim and fenoxaprop.

| CpdA | fenoxaprop | | | |
|---|---|---|---|---|
| Dose | 0 | 15 | 30 | 60 |
| 0 | 0 | 0 | 0 | 0 |
| 15 | 0 | 20 | 30 | 30 |
| 30 | 30 | 40 | 50 | 50 |
| 60 | 30 | 90 | 80 | 80 |

TABLE 3

Post-emergence treatment of LEFCH with various mixtures of pyribenzoxim and bentazone.

| CpdA | bentazone | | | |
|---|---|---|---|---|
| Dose | 0 | 375 | 750 | 1500 |
| 0 | 0 | 0 | 20 | 20 |
| 15 | 0 | 30 | 40 | 70 |
| 30 | 30 | 50 | 50 | 70 |
| 60 | 30 | 80 | 100 | 100 |

TABLE 4

Post-emergence treatment of LEFCH (2 leaf) with various mixtures of pyribenzoxim and bensulfuron.

| CpdA | bensulfuron | | |
|---|---|---|---|
| Dose | 0 | 25 | 50 |
| 0 | 0 | 0 | 0 |
| 15 | 50 | 100 | 100 |

TABLE 5

Post-emergence treatment of LEFCH (2 leaf) with various mixtures of pyribenzoxim and oxadiargyl.

| CpdA | oxadiargyl | | | |
|---|---|---|---|---|
| Dose | 0 | 10 | 20 | 40 | 80 |
| 0 | 0 | 0 | 0 | 0 | 70 |
| 7.5 | 30 | 80 | 80 | 70 | 100 |
| 15 | 50 | 90 | 100 | 100 | 100 |

TABLE 6

Post-emergence treatment of LEFCH (2 leaf)
with various mixtures of pyribenzoxim and benzofenap.

| CpdA | benzofenap | | |
|---|---|---|---|
| Dose | 0 | 600 | 1200 |
| 0 | 0 | 10 | 20 |
| 7.5 | 30 | 80 | 80 |
| 15 | 50 | 100 | 100 |

TABLE 7

Post-emergence treatment of MOOVA (2 leaf)
with various mixtures of pyribenzoxim and fenoxaprop.

| CpdA | fenoxaprop | | | | |
|---|---|---|---|---|---|
| Dose | 0 | 15 | 30 | 60 | 120 |
| 0 | 0 | 0 | 0 | 30 | 70 |
| 15 | 0 | 50 | 70 | 70 | 80 |
| 30 | 70 | 80 | 90 | 100 | 100 |

TABLE 8

Post-emergence treatment of MOOVA (2 leaf)
with various mixtures of pyribenzoxim and oxadiargyl.

| CpdA | oxadiargyl. | | |
|---|---|---|---|
| Dose | 0 | 10 | 20 |
| 0 | 0 | 0 | 0 |
| 15 | 100 | 0 | 80 |
| 30 | 100 | 90 | 90 |

TABLE 9

Post-emergence treatment of MOOVA (2 leaf)
with various mixtures of pyribenzoxim and benzofenap.

| CpdA | benzofenap | | |
|---|---|---|---|
| Dose | 0 | 150 | 300 |
| 0 | 100 | 0 | 0 |
| 7.5 | 100 | 80 | 90 |

TABLE 10

Post-emergence treatment of CYPDI with various
mixtures of pyribenzoxim and fenoxaprop.

| CpdA | fenoxaprop | | |
|---|---|---|---|
| Dose | 0 | 30 | 60 |
| 0 | 0 | 0 | 0 |
| 15 | 60 | 90 | 90 |

TABLE 11

Post-emergence treatment of CYPDI with various mixtures of
pyribeuzoxim and bentazone.

| CpdA | bentazone | | |
|---|---|---|---|
| Dose | 0 | 375 | 750 |
| 0 | 0 | 80 | 80 |
| 7.5 | 0 | 90 | 90 |

It will be seen that the foregoing results demonstrate the presence of synergy in the composition of the invention.

What is claimed is:

1. A composition comprising, in association with an agriculturally acceptable diluent or carrier, (a) a compound of formula (I):

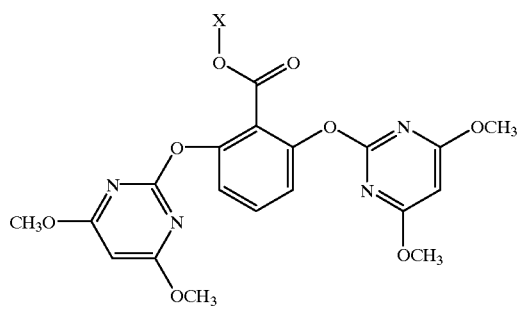

wherein X is a hydrogen atom or a group $(C_6H_5)_2C=N—$, or an agriculturally acceptable salt thereof, and (b) a partner herbicide selected from the group consisting of sulphonyl ureas, bentazone, aryloxyphenoxy propionic acids, pyrazoles and oxadiazoles, wherein the sulphonyl ureas are selected from the group consisting of cinosulfuron, bensulfuron, pyrazolsulfuron, imazosulfuron and azimsulfuron, further wherein the composition contains a synergistic herbicidally effective amount of the combination of (a) and (b).

2. The composition according to claim 1, wherein said agriculturally acceptable salt is an alkali or alkaline earth metal salt.

3. The composition according to claim 1, wherein said aryloxyphenoxy propionic acid is cyhalofop.

4. The composition according to claim 1, wherein said aryloxyphenoxy propionic acid is fenoxaprop.

5. The composition according to claim 1, wherein said aryloxyphenoxy propionic acid is fenoxaprop-P.

6. The composition according to claim 1, wherein said sulfonylurea is bensulfuron.

7. The composition according to claim 1, wherein said sulfonylurea is pyrazosulfuron.

8. The composition according to claim 1, wherein said sulfonylurea is imazosulfuron.

9. The composition according to claim 1, wherein said oxadiazole is oxadiargyl.

10. The composition according to claim 1, wherein the weight ratio of (a) the compound of formula (I) or agriculturally acceptable salt thereof to (b) the partner herbicide ranges from about 1:800 to about 200:1.

11. The composition according to claim 10, wherein the weight ratio of (a) to (b) ranges from about 1:250 to about 20:1.

12. The composition according to claim 11, wherein the weight ratio of (a) to (b) ranges from about 1:40 to about 8:1.

13. The composition according to claim 1, wherein X is $(C_6H_5)_2C=N—$ and the partner herbicide is selected from the group consisting of cyhalofop, fenoxaprop, fenoxaprop-P, bensulfuron, pyrazosulfuron, imazosulfuron, bentazone, benzofenap and oxadiargyl.

14. The composition according to claim 1, wherein the combination of (a) and (b) comprises 0.05 to 90% by weight of said composition.

15. A method for controlling the growth of weeds at a locus which comprises applying to said locus a synergistic herbicidally effective amount of a composition comprising (a) a compound of formula (I):

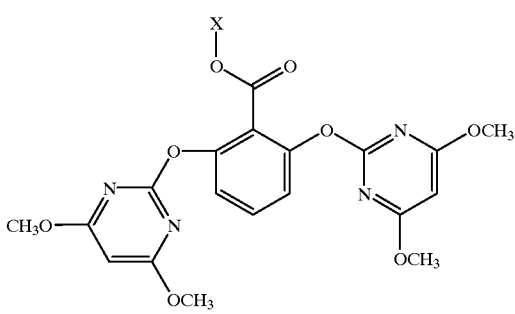

(I)

wherein X is a hydrogen atom or a group $(C_6H_5)_2C=N—$, or an agriculturally acceptable salt thereof, and (b) a partner herbicide selected from the group consisting of sulphonyl ureas, bentazone, aryloxyphenoxy propionic acids, pyrazoles and oxadiazoles, wherein the sulphonyl ureas are selected from the group consisting of cinosulfuron, bensulfuron, pyrazolsulfuron, imazosulfuron and azimsulfuron.

16. The method according to claim 15, wherein said agriculturally acceptable salt is an alkali or alkaline earth metal salt.

17. The method according to claim 15, wherein said partner herbicide is an aryloxyphenoxy propionic acid.

18. The method according to claim 17, wherein said aryloxyphenoxy propionic acid is cyhalofop.

19. The method according to claim 17, wherein said aryloxyphenoxy propionic acid is fenoxaprop.

20. The method according to claim wherein said aryloxyphenoxy propionic acid is fenoxaprop-P.

21. The method according to claim 15, wherein said partner herbicide is a sulfonylurea.

22. The method according to claim 21, wherein said sulfonylurea is bensulfuron.

23. The method according to claim 21, wherein said sulfonylurea is pyrazosulfuron.

24. The method according to claim 21, wherein said sulfonylurea is imazosulfuron.

25. The method according to claim 15, wherein said partner herbicide is oxadiargyl.

26. The method according to claim 15, wherein from 5 g to 200 g per hectare of (a) the compound of formula (I) or agriculturally acceptable salt thereof, and from 1 g to 4000 g per hectare of (b) the partner herbicide are applied to said locus.

27. The method according to claim 26, wherein from 10 g to 100 g per hectare of (a) and from 5 g to 2500 g per hectare of (b) are applied to said locus.

28. The method according to claim 27, wherein from 30 g to 80 g per hectare of (a) and from 10 g to 1200 g per hectare of (b) are applied to said locus.

29. The method according to claim 15, wherein said locus is an area for the growth of a crop.

30. The method according to claim 29, wherein said crop is a rice crop.

31. The method according to claim 15, wherein said composition is applied to said locus by post-emergence application.

32. A product for simultaneous, separate or sequential application in controlling the growth of weeds comprising (a) a compound of formula (I):

(I)

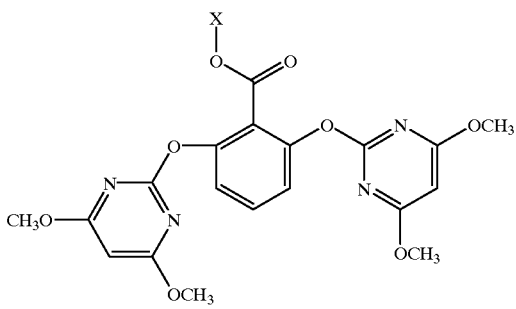

wherein X is a hydrogen atom or a group $(C_6H_5)_2C=N—$, or an agriculturally acceptable salt thereof, and (b) a partner herbicide selected from the group consisting of sulphonyl ureas, bentazone, aryloxyphenoxy propionic acids, pyrazoles and oxadiazoles, wherein the sulphonyl ureas are selected from the group consisting of cinosulfuron, bensulfuron, pyrazolsulfuron, imazosulfuron and azimsulfuron, further wherein the product contains a synergistic herbicidally effective amount of the combination of (a) and (b).

33. The composition according to claim 1, wherein X is H and the partner herbicide is chosen from cyhalofop, fenoxaprop, fenoxaprop-P, bensulfuron, pyrazosulfuron, imazosulfuron, bentazone, benzofenap and oxadiargyl.

34. The method according to claim 15, wherein said partner herbicide is an oxadiazole.

35. The composition according to claim 1, wherein X is $(C_6H_5)_2C=N—$ and the partner herbicide is bentazone or benzofenap.

36. The method according to claim 15, wherein X is $(C_6H_5)_2C=N—$ and the partner herbicide is bentazone or benzofenap.

* * * * *